US008795231B2

(12) United States Patent
Chong et al.

(10) Patent No.: US 8,795,231 B2
(45) Date of Patent: Aug. 5, 2014

(54) AUTOMATED RESERVOIR FILL SYSTEM

(75) Inventors: Colin A. Chong, Burbank, CA (US);
Arsen Ibranyan, Glendale, CA (US);
Eric M. Lorenzen, Granada Hills, CA
(US); Edgardo C. Halili, Santa Clarita,
CA (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

(21) Appl. No.: 13/467,950

(22) Filed: May 9, 2012

(65) Prior Publication Data

US 2012/0289900 A1 Nov. 15, 2012

Related U.S. Application Data

(60) Provisional application No. 61/484,590, filed on May 10, 2011.

(51) Int. Cl.
*A61M 1/00* (2006.01)
*B67C 3/00* (2006.01)
*A61M 5/32* (2006.01)

(52) U.S. Cl.
USPC ........... 604/122; 604/413; 604/414; 141/329; 141/330

(58) Field of Classification Search
USPC ............ 604/411–416, 122–125, 129; 141/18, 141/29, 82, 325, 329–330
See application file for complete search history.

(56) References Cited

U.S. PATENT DOCUMENTS

| | | | |
|---|---|---|---|
| 4,755,173 A | 7/1988 | Konopka et al. | |
| 5,391,250 A | 2/1995 | Cheney, II et al. | |
| 5,485,408 A | 1/1996 | Blomquist | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,500,239 B2 * | 12/2002 | Castellano et al. | ............. 95/247 |
| 6,544,212 B2 | 4/2003 | Galley et al. | |
| 6,558,351 B1 | 5/2003 | Steil et al. | |
| 6,591,876 B2 | 7/2003 | Safabash | |
| 6,641,533 B2 | 11/2003 | Causey, III et al. | |

(Continued)

*Primary Examiner* — Nicholas Lucchesi
*Assistant Examiner* — Weng Lee
(74) *Attorney, Agent, or Firm* — Medtronic Minimed, Inc.

(57) ABSTRACT

An automated reservoir filling system for a portable medical device is disclosed. The system includes a vial sealed by a septum partially filled with a liquid and a gas occupying a headspace. The system further includes a reservoir with a volume defined between a reservoir septum and a plunger head. The plunger head is coupled to a plunger arm which is further coupled to a drive system. Further included is a transfer system with a vial end that pierces the vial septum and remains in contact with the liquid, and a reservoir end that pierces the reservoir septum and remains in the reservoir volume. A controller coupled to the drive system to actuates the drive system automatically drawing fluid from the vial to the reservoir through the degas system.

10 Claims, 5 Drawing Sheets

(56) References Cited

U.S. PATENT DOCUMENTS

| | | |
|---|---|---|
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2007/0123819 A1 | 5/2007 | Mernoe et al. |
| 2008/0269713 A1* | 10/2008 | Kavazov ............... 604/413 |
| 2010/0160861 A1 | 6/2010 | Causey, III et al. |
| 2012/0035543 A1* | 2/2012 | Kamen et al. ........... 604/113 |

* cited by examiner

AUTOMATED RESERVOIR FILL SYSTEM

RELATED APPLICATIONS

This application claims priority to U.S. Provisional Patent Application Ser. No. 61/484,590 filed on May 10, 2011 which is specifically incorporated by reference herein in its entirety.

FIELD OF THE INVENTION

Embodiments of the present invention relate to systems and methods generally related to filling reservoirs for portable medical devices.

BACKGROUND OF THE INVENTION

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have been configured in implantable devices, which are implanted inside of the body of a patient. External pump type delivery devices include devices designed for use in a stationary location, such as a hospital, a clinic, or the like, and further include devices configured for ambulatory or portable use, such as devices designed to be carried by a patient, or the like. External pump-type delivery devices may contain reservoirs of fluidic media, such as, but is not limited to, insulin.

Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump-type delivery devices may be connected in fluid-flow communication to a patient or patient-user, for example, through suitable hollow tubing. The hollow tubing may be connected to a hollow needle that is designed to pierce the skin and deliver an infusion medium to the patient or patient-user. Alternatively, the hollow tubing may be connected directly to the patient or patient-user through a cannula or set of micro-needles.

In contexts in which the hollow tubing is connected to the patient-user through a hollow needle that pierces skin of the user-patient, a manual insertion of the needle into the patient-user can be somewhat traumatic to the user-patient. Accordingly, insertion mechanisms have been made to assist the insertion of a needle into the user-patient, whereby a needle is forced by a spring to move quickly from a retracted position into an extended position. As the needle is moved into the extended position, the needle is quickly forced through the skin of the user-patient in a single, relatively abrupt motion that can be less traumatic to certain user-patients as compared to a slower, manual insertion of a needle. While a quick thrust of the needle into the skin of the user-patient may be less traumatic to some user-patients than a manual insertion, it is believed that, in some contexts, some user-patients may feel less trauma if the needle is moved a very slow, steady pace.

Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method,"; and U.S. patent application Ser. No. 11/211,095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

In addition to difficulties with insertion of infusion sets the filling of a reservoir for an external pump system can provide further anxiety or consternation for some user-patients. The process of filling a reservoir before installing the reservoir in an external infusion pump can be time consuming and difficult for some user-patients. In an embodiment where the reservoir is filled with insulin a number of issues can complicate the filling of a reservoir. These complications have a potential to cause issues from relatively benign aesthetic issues to potentially inaccurate delivery of insulin from the infusion system.

Pump-type delivery devices can allow accurate doses of insulin to be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump-type delivery devices have become an important aspect of modern medical treatments of various types of medical conditions, such as diabetes. As pump technologies improve and as doctors and patient-users become more familiar with such devices, the popularity of external medical infusion pump treatment increases and is expected to increase substantially over the next decade.

SUMMARY OF THE DISCLOSURE

A system to automatically fill a reservoir for a portable medical device is disclosed. The system includes a vial sealed with a septum that is partially filled with a liquid and a gas occupying a headspace. The system further includes a reservoir with a reservoir volume defined between a reservoir port sealed with a reservoir septum and a plunger head. The plunger head coupled to a plunger arm and the plunger arm coupled to a drive system defined to move the plunger arm within a chamber. The transfer system further has a vial end defined to pierce the vial septum and remain in contact with the liquid and a reservoir end defined to pierce the reservoir septum and remain in the reservoir volume. A degas system is included with the system to elevate the temperature of the liquid before the liquid enters the reservoir. A controller coupled to the drive system actuates the drive system to automatically draw the fluid from the vial to the reservoir through the degas system.

In another embodiment a different system to automatically fill a reservoir for a portable medical device is disclosed. The system includes a vial sealed with a septum partially filled with a liquid and a gas occupying a headspace. A reservoir is included with the system, the reservoir having a reservoir volume defined between a reservoir port sealed with a septum and a plunger head, the plunger head coupled to a plunger arm, the plunger arm coupled to a drive system defined to move the plunger arm within a chamber. The system further includes a first degas system having a temperature system to elevate the liquid temperature before the liquid enters the reservoir. A second degas system is included with the system. The second gas system includes a valve end coupled to a check valve, the second degas system further having a headspace end defined to pierce the vial septum, the headspace end being positioned in the headspace, the check valve further being coupled to a vacuum system. The system further includes a transfer system with a vial end defined to pierce the vial septum and remain in contact with the liquid and a reservoir end defined to pierce the reservoir septum and remain in the reservoir volume. A controller coupled to the drive system and the valved system is included with the system. The controller actuates the valved system to automatically draw a partial vacuum within the vial for a period of time before the drive system is automatically actuated to draw the fluid from the vial to the reservoir.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

Figure 1A:
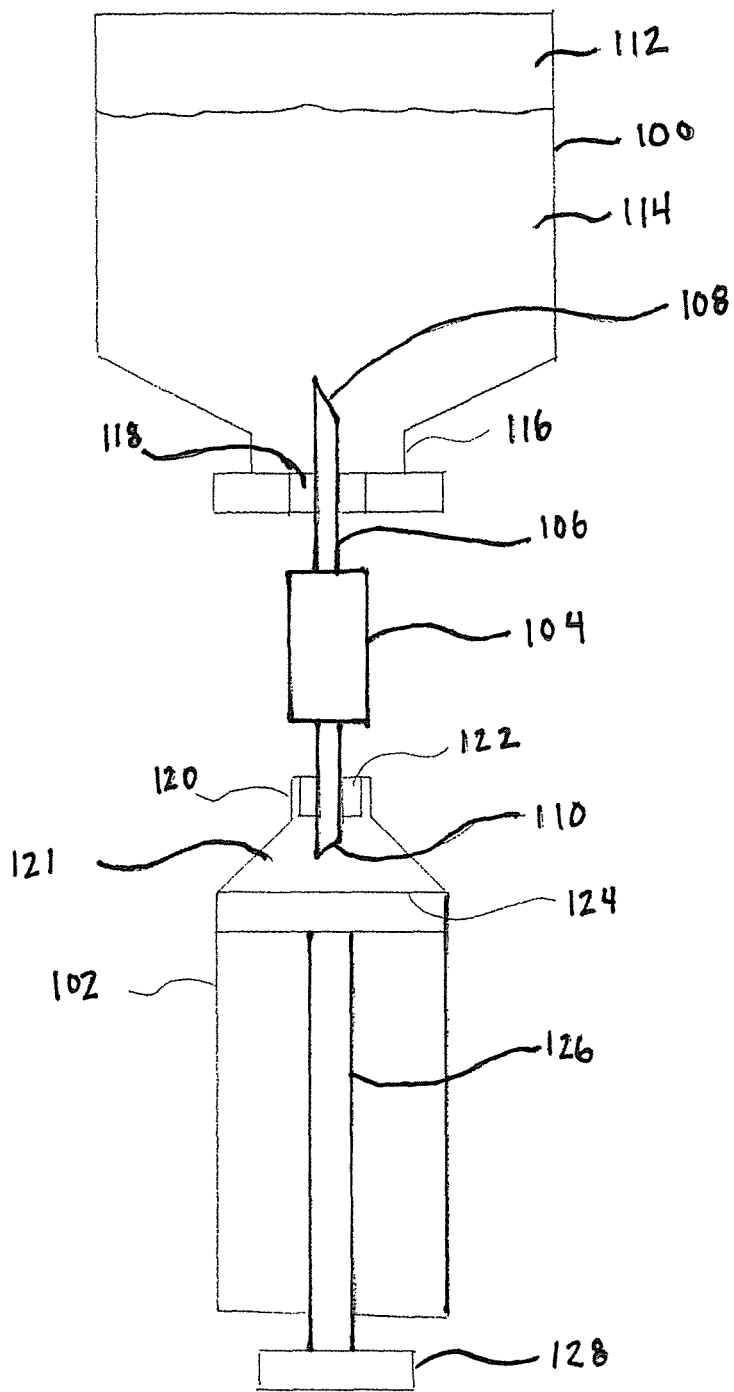
FIGS. 1A and 1B are exemplary illustrations of components of an automated reservoir fill system, in accordance with embodiments of the present invention.

As shown in the drawings with the associated description the invention relates to the automated transfer between a vial and a reservoir while minimizing the likelihood that bubbles will appear in the reservoir. Accordingly, the invention utilizes some commonly sourced disposable medical supplies such as vials containing fluid media such as, but not limited to insulin. The manual transfer of fluid media from a vial to the reservoir has generated discussion regarding simplification of the process along with improvements to minimize formation of air bubbles within the reservoir.

In some embodiments the reservoir is used with an external infusion pump where it may take an external infusion pump as long as three days to exhaust the fluid contained in a reservoir. Once exhausted, the empty reservoir is discarded and a new reservoir must be filled and installed into the external infusion pump. In other embodiments larger or smaller reservoirs may be used along with various infusion rates to shorten or prolong the rate at which reservoirs must be discarded and filled. In embodiments where insulin is being infused the insulin may be stable in the reservoir for up to three days. After three days the efficacy of the insulin may decrease thereby resulting in ineffective dosing and treatment.

The insulin used to fill the reservoir is generally supplied in standard insulin vials, such as those used by individuals using periodic injection. Accordingly, the vial of insulin used to fill the reservoir most likely contains enough insulin to fill multiple reservoirs. To prolong efficacy of insulin within the vial it is common to store the vial at refrigerated temperatures. Refrigeration in conjunction with air trapped in the headspace above the insulin contributes to air becoming dissolved within the insulin. If the insulin is not properly degassed it is possible for air dissolved in insulin to come out of solution with an increase in temperature or a decrease in pressure. A simple method to partially degas the chilled insulin is to simply let the insulin warm up to room temperature. While instruction manuals, user guides and quick reference guides can all recommend letting insulin reach room temperature before filling a reservoir, it can take an unacceptable amount of time for a vial to reach room temperature. With hectic work and social lives many people do not have the time or patience to wait for a vial to reach room temperature and simply fill a reservoir with insulin straight from the refrigerator or possibly slightly warmed via a variety of methods.

Thus, while a reservoir filled with chilled insulin may be bubble free, as the insulin warms to room temperature the dissolved gasses may come out of solution resulting in a reservoir with small air bubbles. In some instances the air bubbles pose no hazard and can be viewed as an aesthetic issue. In other instances, if enough air comes out of solution a large air bubbles can introduce elasticity in the infusion system thereby compromising treatment if proper dosages are not being administered. Additionally, air bubbles may also pose a safety risk to a user. Accordingly, an automated reservoir fill system that is able to degas the fluid to compensate for temperature differences could greatly simplify and streamline reservoir filling while mitigating a potential pitfall of air bubbles in the infusion system.

Figure 1B:
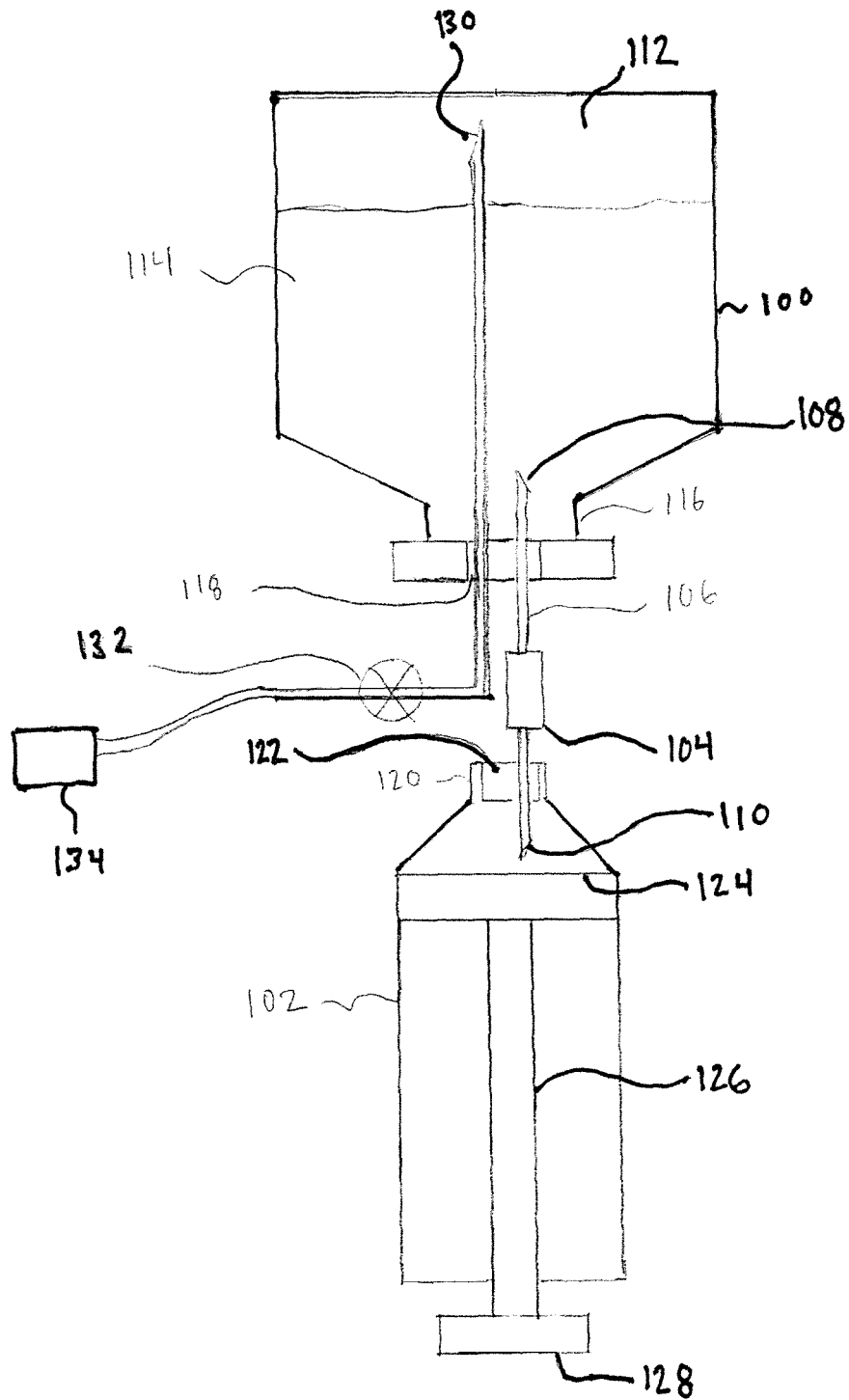

FIGS. 1A and 1B are exemplary illustrations of components of an automated reservoir fill system in accordance with embodiments of the present invention. Both FIGS. 1A and 1B include a vial 100 partially filled with a fluid 114 leaving a headspace 112. Each vial 100 has a vial port 116 sealed with a vial septum 118. The vial septum 118 may be configured to prevent fluid flow out of the vial port 116 and in some embodiments is a self-sealing septum. Additionally, FIGS. 1A and 1B both include a reservoir 102 having a reservoir volume 121 defined between a reservoir port 120 sealed by a reservoir septum 122 and a plunger head 124. The reservoir septum 122 may be configured to prevent fluid flow out of the reservoir port 120 and in some embodiments is a self-sealing septum. A plunger arm 126 having a plunger base 128 is removably coupled to the plunger head 124. The reservoir volume 121 may be increased or decreased by moving the plunger head 124 within the reservoir 102 via the plunger base 128.

A transfer system 106 includes a first degas system 104, a vial end 108 and a reservoir end 110. Both the vial end 108 and the reservoir end 110 are defined to pierce the vial septum 118 and reservoir septum 122 respectively. The transfer system 106 enables fluid transfer from the vial 100 to the reservoir 102 through the first degas system 104. As illustrated in FIG. 1A, to prepare the system for fluid transfer between the vial 100 and the reservoir 102, the vial 100 is positioned so the headspace is substantially opposite the vial port 116. The vial end 108 is inserted through the vial septum 118 and positioned within the fluid 114. Similarly, the reservoir end 110 pierces the reservoir septum 122 and is positioned within the reservoir volume 121. Elements shown in FIGS. 1A and 1B are intended to be simplified illustration and should not be considered limiting. For example, the transfer system 106 should not be construed as only being a straight pass through the degas system 104. In other embodiments the vial end 108 and the reservoir end 110 may be connected to flexible or rigid tubing that allows the reservoir to be in various positions rather than in-line with the vial as shown in FIGS. 1A and 1B.

FIG. 1B further includes a second degas system that includes a vacuum 134 connected to a check valve 132 that is connected to a headspace end 130. The headspace end 130 is defined to pierce the vial septum and be positioned within the headspace 112. The second degas system allows a partial vacuum to be drawn within the vial 100 thereby further degassing the fluid 114. In some embodiments the check valve 132 opens and allows the vacuum 134 to draw a partial vacuum within the vial. Various embodiments allow the vacuum to be drawn for between five and thirty seconds to degas the fluid. The check valve 132 can be closed before the fluid 114 is transferred from the vial 100 to the reservoir 102 via the transfer system 106. As will be discussed later the transfer system 106 can contribute to further degassing of the fluid 114 before it enters the reservoir 102.

In another embodiment of FIG. 1B the vacuum 134 (run in reverse) and the check valve 132 are used to pressurize the headspace 112 within the vial 100. The pressurization of the headspace 112 can assist in transferring fluid 114 from the vial 100 into the reservoir 102. In such embodiments the degas system 104 may be modified to accommodate any additional degassing of the fluid required to compensate for any increase in dissolved gas from the pressurization of the headspace.

Figure 2A:
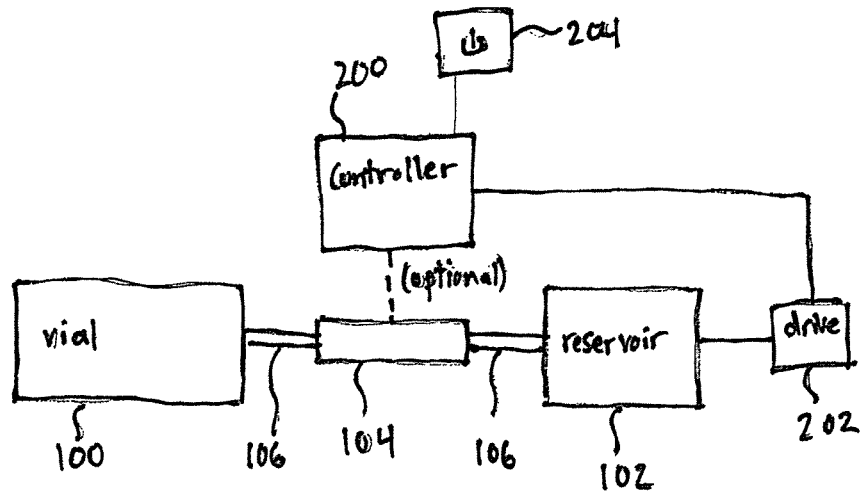
FIGS. 2A and 2B are simplified block diagrams illustrating automation of a reservoir filling system in accordance with embodiments of the present invention.
Figure 2B:
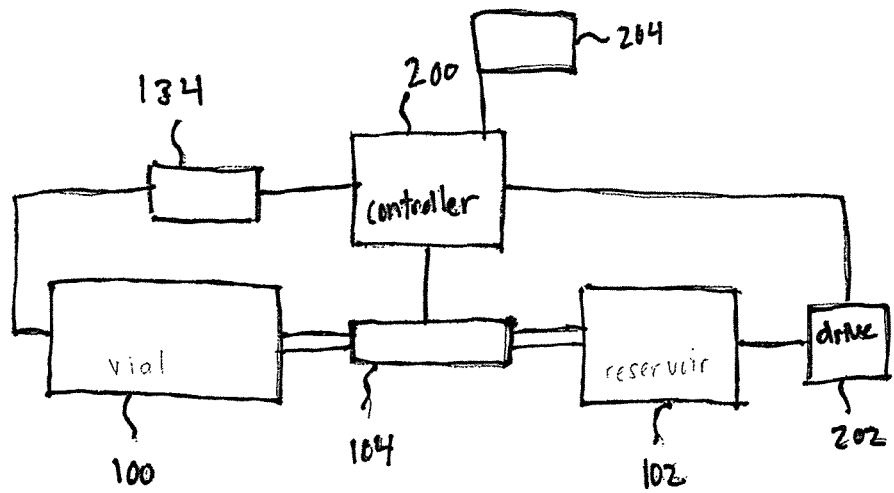

FIGS. 2A and 2B are simplified block diagrams illustrating automation of a reservoir filling system in accordance with embodiments of the present invention. Automation of the elements shown in FIGS. 1A and 1B can be accomplished using a controller 200 to effectively time and execute degassing and filling the reservoir 102 from the vial 100. In FIG. 2A the controller is coupled to a drive 202 and the drive 202 is coupled with the plunger base 128. Activation of the controller initiates the drive 202 to pull the plunger base 128 thereby drawing fluid from the vial 100 through the degas system 104 and into the reservoir 102. In FIG. 2B the controller 200 is coupled to the drive 202 along with the vacuum 134 and vacuum 134 is coupled with apparatus described in FIG. 1B to draw a vacuum within the vial 100. In these embodiments the controller 200 activates the vacuum drawing a vacuum within the vial for a specified period of time. Once the specified time period has lapsed, the controller 200 activates the drive 202 in order to draw degassed fluid from the vial 100 through the degas system 104 and into the reservoir 102.

In some embodiments the controller 200 is a purely mechanical device relying on resettable or rewindable springs for power. Accordingly, the drive 202 would be mechanical and releasing of a spring or other mechanical energy storage device would initiate an automated fill process in accordance with either FIG. 2A or 2B. In other embodiments the controller 200 may be coupled to an electrical power supply such as a battery, solar cells or even plugged into a wall socket. In these embodiments feedback loops and additional sensors may be used to further refine performance of the automated fill system.

Figure 3A:
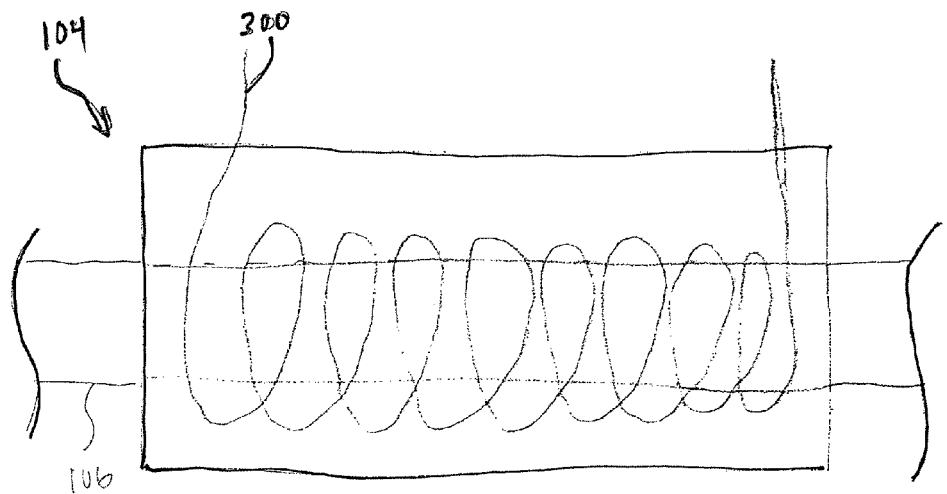
FIGS. 3A-3C are schematic illustrations of various degassing systems for use with the automated reservoir filling system, in accordance with embodiments of the present invention.
Figure 3B:
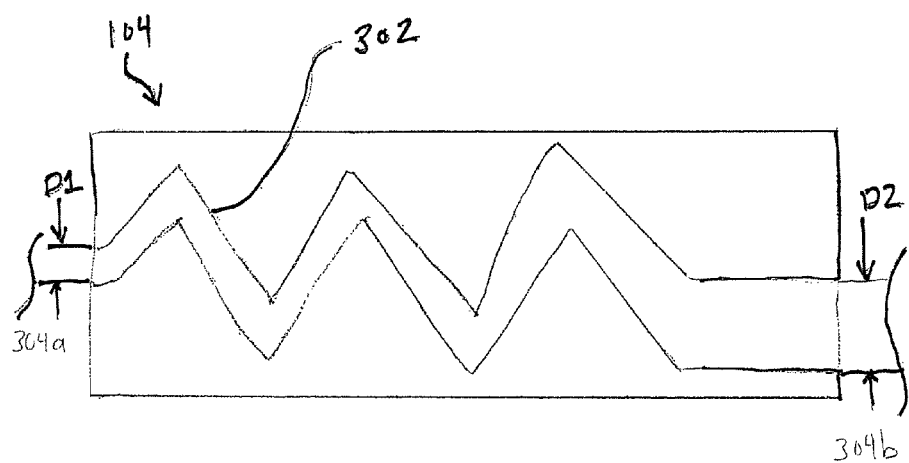
Figure 3C:
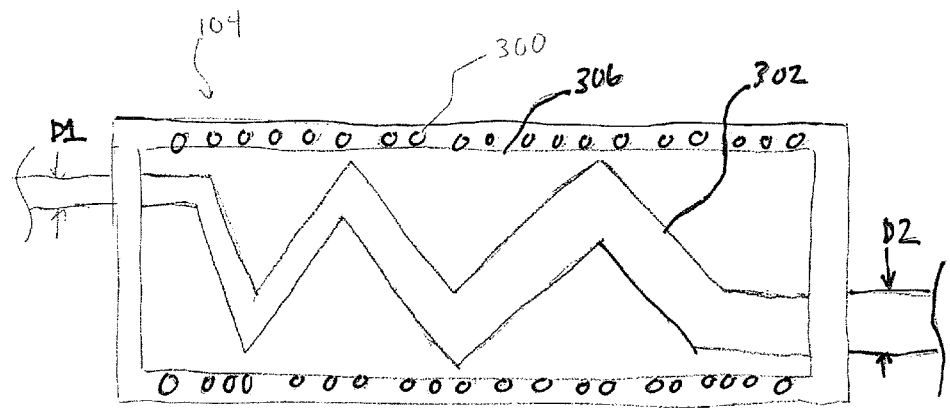

FIGS. 3A-3C are schematic illustrations of various degassing systems for use with the automated reservoir filling system, in accordance with embodiments of the present invention. FIG. 3A shows the degas system 103 where the transfer system 106 passes through a heating element 300. The heating element 300 is within close proximity to the transfer system 106 so as to warm the fluid, thereby degassing the fluid, as the fluid traverses through the degas system. Accordingly, the length of the degas system can be influenced by the maximum increase in temperature desired, the rate and volume at which fluid is drawn through the degas system, or the energy supplied to the heating element 300. Energy may be supplied to the heating element 300 in the form of electrical, chemical, magnetic, mechanical or the like. While FIG. 3A shows the heating element 300 wrapped around the transfer system 106, other embodiments could have heating elements placed in close proximity but not completely surrounding the transfer system 106.

FIG. 3B is a schematic illustrating a degas system 104 that does not rely on auxiliary heating elements. This embodiment can be used in purely mechanical systems because it does not rely on external power to degas the fluid. In this embodiments the fluid enters the degas system 104 via an inlet 304a with a first diameter D1. The fluid flows through a temperature path 302 and eventually exits via outlet 304b with a second diameter D2. Depending on the desired increase in temperature the change in diameters can be determined for a desired flow rate. In another embodiment similar to FIG. 3B, if D1 and D2 remain the same, it would be possible to obtain degassing of the fluid via an increase in temperature via a convoluted temperature pathway 302 via friction with the pathway. In the embodiments discussed with FIG. 3B the design of the temperature pathway 302 along with potential changes in diameter provide degassing as the fluid is drawn through the degas system 104. This can be highly advantageous in designing and building robust purely mechanical systems for use in areas with unreliable power such as remote areas or emergency medical situations following natural disasters.

FIG. 3C is a cross-section schematic illustration of an exemplary degas system 104, in accordance with embodiments of the present invention. The degas system 104 in FIG. 3C is a combination of the degas systems in FIGS. 3A and 3B. The heating element 300 is shown as if it was a cross-sectional view wrapped around a volume 306 containing the temperature path 302. The temperature path 302 is defined with an inlet having a diameter D1 and an outlet having a diameter D2 that can degas fluid via temperature increase as the fluid is pulled through the degas system. In addition to the temperature increase from the temperature path 302, the heating element 300 can further increase the temperature of the fluid to provide additional degassing. As described with FIG. 3B, some embodiments may rely on friction between the fluid and a convoluted temperature path 302 to increase the temperature while D1 and D2 remain the same. In some embodiments a maximum temperature increase is determined so as to not take temperature sensitive fluid beyond a specified preferred temperature. Thus, specific design of D1 and D2 in conjunction with or without a temperature pathway 302 can result in a maximum temperature increase. The maximum temperature increase can help preserve efficacy of temperature sensitive medicaments while they are being transferred into the reservoir.

The embodiment shown in FIG. 3C is well suited for an automated reservoir filling system with feedback to the controller as described in FIG. 2B. In some embodiments optional temperature sensors detect the temperature of the fluid as it enters and exits the degas system. Based on the fluid being infused, the controller is programmed with an ideal degassing temperature. The controller is further programmed with instructions to determine if the maximum temperature change from the temperature path 302 and change from D1 to D2 will be sufficient to reach the ideal degassing temperature. If necessary, the controller will further be programmed to activate the heating element 300 to compensate for any shortcomings of the temperature path 302.

In other embodiments, the controller is able to control the rate at which drive system pulls fluid through the degas system 104. In these embodiments it may not be necessary to include the change in diameter from D1 to D2 or the temperature path 302. Being able to control the drive system, and therefore the rate fluid is pulled through the degas system 104, in conjunction with heating element 300, and further in conjunction with temperature sensors at the input and output of the degas system 104 means the programmer can ensure the fluid achieves an ideal degassing temperature.

Figures 4A, 4B:
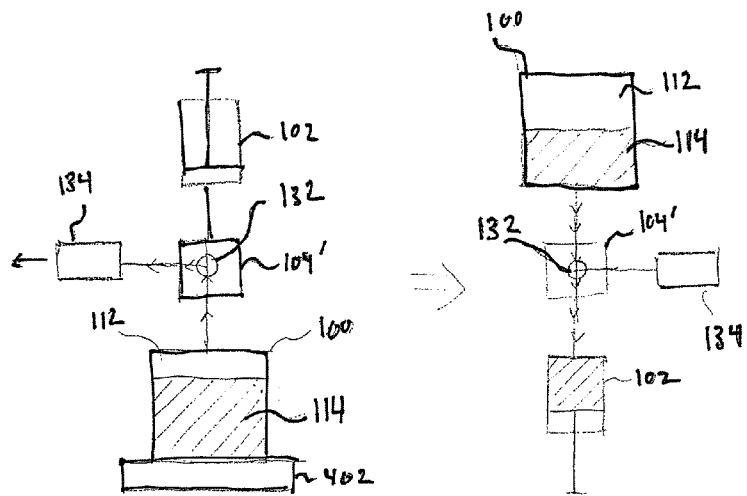
FIGS. 4A and 4B are simplified illustrations of an alternative embodiment for an automated reservoir filling system, in accordance with embodiments of the present invention.

FIGS. 4A and 4B are simplified illustrations of an alternative embodiment for an automated reservoir filling system, in accordance with embodiments of the present invention. FIG. 4A shows a reservoir 102 coupled with a transfer system 106' that include a check valve 132. Also coupled to the transfer system 106' is a vial 100 partially filled with fluid 114 and having head space 112. The vial 100 is in contact with an agitator 402. The agitator 402 can assist in degassing the fluid 114 by vibrating the fluid. Though not shown in FIGS. 1A-1B and 2A-2B, an agitator 402 can be incorporated into those systems to further improve degassing. In some embodiments the agitator 402 is a plate or panel that vibrates while in other embodiments the agitator 402 is an ultrasonic emitter. In still other embodiments other electro-mechanical, mechanical, acoustic systems or combinations thereof may be used as the agitator 402. The transfer system 106' of FIG. 4A is similar to the transfer system 106 in FIG. 1A. In addition to the transfer system 106 in FIG. 1A, transfer system 106' includes a check valve to incorporate the vacuum system 134. This embodiment reduces the number of elements piercing the respective vials as shown in FIG. 1B.

To degas the fluid 114 using the system shown in FIGS. 4A and 4B, the vial 114 is placed on the agitator and coupled to the transfer system 106'. The reservoir 102 is also coupled with the transfer system 106'. In some embodiments, the check valve 132 is opened enabling fluid flow between the vial 100 and the reservoir 102. A controller is activated so the agitator is activated while air in the head space 112 is drawn through the transfer system 106' into the reservoir 102. This creates a partial vacuum in the headspace 112 and degasses the fluid 114. After a sufficient period of time has passed to degas the fluid 114, the check valve 132 positioned to maintain the partial vacuum in the vial 100 while allowing the gas drawn into the reservoir 102 to be expelled. The controller (not shown for simplicity) then rotates the entire apparatus to the position shown in FIG. 4B. This places the vial 100 above the reservoir 102 and the fluid 114 in contact with the transfer system 106'. The controller positions the check valve 132 to enable fluid flow into the reservoir 102 and the drive system draws the plunger of the reservoir pulling degassed fluid from the vial 100 through the transfer system 106' into the reservoir 102.

In other embodiments, an optional vacuum 134 is further coupled to the check valve 132 thereby requiring actuation of the reservoir plunger once, only when fluid is transferred from the vial 100 to the reservoir 102. The use of the optional vacuum 134 can ensure a more consistent partial vacuum is drawn thereby providing more thorough degassing.

The descriptions provided above are intended to be exemplary. Multiple embodiments of the degas system were described and the respective embodiments may be implemented with at least any of the systems discussed. Additionally, in other embodiments multiple degas systems with or without an agitator may be used in serial or in parallel to degas the fluid. Furthermore, multiple automation techniques were described. The automation techniques are intended to be construed as exemplary rather than restrictive. Combinations of mechanical, electro-mechanical and other forms of powered automation should be considered within the scope of the disclosure. While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A system to automatically fill a reservoir for a portable medical device comprising:

a vial having a vial volume partially filled with a liquid and a gas, the gas occupying a headspace, the vial further having a vial port sealed with a vial septum;

a reservoir having a reservoir volume defined between a reservoir port and a plunger head, the plunger head coupled to a plunger arm, the plunger arm coupled to a drive system defined to move the plunger arm within a chamber, the reservoir port being sealed by a reservoir septum;

a first degas system having a temperature system to elevate the liquid temperature before the liquid enters the reservoir;

a second degas system having a valve end coupled to a check valve, the second degas system further having a headspace end defined to pierce the vial septum, the headspace end being positioned in the headspace, the check valve further being coupled to a vacuum system;

a transfer system having a vial end defined to pierce the vial septum and remain in contact with the liquid, the transfer system further having a reservoir end defined to pierce the reservoir septum and remain in the reservoir volume;

a controller coupled to the drive system, and the second degas system, the controller defined to actuate the second degas system to automatically draw a partial vacuum within the vial for a period of time before the drive system is automatically actuated to draw the fluid from the vial to the reservoir.

2. A system as defined in claim 1 requiring no electrical power, wherein the controller, the first degas system, the second degas system and the drive system are entirely mechanical systems.

3. A system as defined in claim 2, wherein the first degas system is defined as a pathway calculated to increase the temperature of the fluid by a maximum amount via friction.

4. A system as defined in claim 2, wherein the first degas system is defined as a pathway with varying cross-sectional area to induce a maximum change of temperature of the fluid.

5. A system as defined in claim 1 further comprising:
a power source and heating elements incorporated into the first degas system.

6. A system as defined in claim 5, wherein the first degas system is defined as a pathway calculated to increase the temperature of the fluid by a maximum amount via heat exchange from operation of the heating elements 7. A system as defined in claim 5, wherein the power source further powers a feedback system associated with the controller, the feedback system having a temperature sensor that determines the fluid temperature in the vial.

8. A system as defined in claim 7, wherein the heating elements are defined along a pathway calculated to increase the temperature of the fluid by a maximum amount via friction, the heating elements being activated when the feedback system determines that fluid heating in addition to friction heating is required to properly degas the fluid.

9. A system as defined in claim 5, wherein the heating elements are defined along a pathway calculated to increase the temperature of the fluid by a maximum amount via a change in cross-sectional area, the heating elements being active when the feedback system determines that fluid heating in addition to the maximum change via change in cross-sectional area is required to properly degas the fluid.

10. A system as defined in claim 5, wherein the system further powers a vibration generation device, such that activation of the vibration generation device degases the fluid within the vial.

* * * * *